United States Patent [19]

Bombardelli et al.

[11] Patent Number: 5,665,365
[45] Date of Patent: Sep. 9, 1997

[54] FORMULATIONS CONTAINING COUMARINS AND THE USE THEREOF IN THE PHARMACEUTICAL AND COSMETIC FIELDS

[75] Inventors: Ezio Bombardelli; Aldo Cristoni; Paolo Morazzoni, all of Milan, Italy

[73] Assignee: Indena S.p.A., Milan, Italy

[21] Appl. No.: 498,867

[22] Filed: Jul. 6, 1995

[30] Foreign Application Priority Data

Jul. 26, 1994 [IT] Italy ................... MI94A1590

[51] Int. Cl.$^6$ .................... A61K 31/35; A61K 31/70
[52] U.S. Cl. .................... 424/401; 424/195.1; 424/59; 424/60
[58] Field of Search ................ 424/195.1, 401, 424/59, 60; 514/855, 863, 864, 844, 846, 944, 951

[56] References Cited

U.S. PATENT DOCUMENTS

| | | | |
|---|---|---|---|
| 4,925,871 | 5/1990 | Gabetta et al. | 514/453 |
| 4,963,527 | 10/1990 | Bombardelli et al. | 514/25 |

FOREIGN PATENT DOCUMENTS

| | | |
|---|---|---|
| 0 275 224 | 7/1988 | European Pat. Off. . |
| 0 348 781 | 1/1990 | European Pat. Off. . |
| 0 412 300 | 2/1991 | European Pat. Off. . |
| 589 294 | 5/1981 | Germany . |

OTHER PUBLICATIONS

Phlebologie (Germany), 1944, "Hostettmann K. et al. Zu 'Inhaltsstoffen und Pharmakologie Pflanzicher Venemittel"; p. 72, col. 1, para. 3 —p. 73, col. 3, para. 2.

*Primary Examiner*—Thurman K. Page
*Assistant Examiner*—Sharon Howard
*Attorney, Agent, or Firm*—Pennie & Edmonds

[57] ABSTRACT

The present invention relates to the use of coumarins such as esculoside, esculetin, extracts containing them and mixtures thereof, in combination with dimeric and oligomeric proanthocyanidins, in topical formulations for the treatment of peripheral vasculopathies, including the complications of acute venous stasis, or of the unesthetisms related to capillary alterations, or to improve the cicatrization processes. These coumarins, alone or in combination with proanthocyanidins, are also useful in atopical dermatitis and in the treatment of the haematomas.

23 Claims, No Drawings

FORMULATIONS CONTAINING COUMARINS AND THE USE THEREOF IN THE PHARMACEUTICAL AND COSMETIC FIELDS

TECHNICAL FIELD

The present invention relates to the use of novel formulations for topical use containing combinations of coumarins, such as esculoside, escultin, extracts containing them or mixtures thereof, with dimeric and oligomeric proanthocyanidins for the treatment of peripheral vasculopathies related to an impaired peripheral microcirculation. Moreover, the invention relates to the use of said coumarin derivatives in combination with proanthocyanidins in the cicatrization processes and in the complications of chronic venous stasis (leg heaviness, ulcus cruris) and in the treatment of internal and external hemorrhoids. In a strictly cosmetic field, the combinations are used in the treatment of unesthetisms, including blemishes and cosmetic disfiguration related to superficial capillaries (couperose), rosacea, telangiectasias and the like. It has surprisingly been found that a strong synergism exists between these coumarin derivatives and proanthocyanidins.

BACKGROUND OF THE INVENTION

A number of conditions related to impaired peripheral microcirculation have resisted treatment. These include impairment of arterial and venous circulation, unesthetisms, including cosmetic disfigurements and blemishes, related to impaired capillary permeability and fragility, superficial and deep scars, internal and external hemorrhoids; conditions related to chronic venous stasis, including stasis ulcers and telangiectasias, couperose, and peripheral capillaropathies. In addition there has been a need for a treatment that will improve the rate of healing and reduce scarring following surgery or injury. The present invention addresses both these needs.

SUMMARY OF THE INVENTION

The present invention relates to topical pharmaceutical and cosmetic formulations that include coumarins, such as esculoside, escultin, extracts containing coumarins, and, optionally, proanthocyanidins, such as proanthocyanidin A2, procyanidole oligomers extracted from *Vitis vinifera* and *Camellia sinensis*, and mixtures thereof. The formulations of the present invention can be applied to a subject to increase capillary density of the skin or other tissue. The increase in capillarity is useful in the treatment of peripheral vasculopathies related to impairment of arterial and venous circulation, and of unesthetisms, such as cosmetic disfigurations or blemishes, related to impaired capillary permeability and fragility. In particular, the claimed formulations are useful as treatments for superficial and deep scars, internal and external hemorrhoids, conditions related to chronic venous stasis, such as stasis ulcers and telangiectasias, couperose, and peripheral capillaropathies.

DETAILED DESCRIPTION OF THE INVENTION

The microvasculokinetic activity of esculoside, responsible for many of the properties of the combinations (cicatrizing and antihemorrhoid) was evaluated by non-invasive techniques such as infrared photopulsoplethysmography, Laser-Doppler and video-capillaroscopy which makes it possible to check the districtual microangiotectonic and the capillary morphological changes before and after the treatment with the tested substances. Esculoside induces favorable changes in the capillary density, up to 300% higher than the basal values.

In the combinations according to the invention, the weight ratio of coumarin derivatives to proanthocyanidins preferably ranges from 4:1 to 1:4. For example, combinations of three parts of esculoside and one part of proanthocyanidins (selected from proanthocyanidin A2 and the procyanidole oligomers of a different origin, preferably those extracted from *Vitis vinifera* or *Camellia sinensis*) exert synergistic activities which are qualitatively different from those of the single components. A non-limiting interpretation of this fact is that esculoside increases the proanthocyanidin absorption at the topical level as a consequence of the increase in districtual blood flow, and therefore of water. Particularly synergistic is the modulating activity on the cicatrization process, wherein a stimulation of the tissue restoration and a regular orientation alongside the cicatricial axis are observed, thus preventing the formation of keloids.

Analogously, these combinations are favorably used in the treatment of unesthetisms, including blemishes and cosmetic disfigurations, and on the reduction of the couperose. In the latter case, 20 individuals of both sexes were treated on one side of the face in the temporal-zygomatic area with a 1.5% esculoside and 0.5% of proanthocyanidin A2 formulation and on the other side with placebo. The treatment continued for 60 days twice a day; the evaluation of the intensity of the unesthetism was performed by means of scores and with objective evaluations measuring the colour intensity of the area treated with the combination of the invention compared with that treated with placebo. After the treatment, a 41% reduction in the couperose was observed, using the patient himself as control.

Particularly important is the healing effect of the combinations according to the invention, which effect can be used in plastic surgery as well as in decubitus and venous stasis ulcers. To evaluate the cicatrization effect, patients were selected which had undergone superficial surgery, having wounds of a size suitable to the simultaneous treatment with the combination of the invention and with placebo. For example: cauterized wounds larger than 2 cm, so as to allow, after suturation, the treatment of 1 cm with a placebo formulation and of 1 cm with a formulation containing 1.5% esculoside and 1.5% procyanidole oligomers from *Vitis vinifera*. Immediately after the treatment, the adhesion edges and nearby areas of the wound were checked with a video-capillaroscope (Scopeman-Moritex Video Imaging System, Alpha Strumenti, Milan), fitted with a halogen-light optical probe with 50 to 400×magnifications, measuring the capillary density (number of blood-perfused capillaries per area unit) and evaluating the space orientation of the capillaries and their morphology. Fifteen minutes after the treatment, the capillary density increased by 100% compared with the basal one and with the placebo-treated control. Surprisingly it has been found, and it is a part of the present invention, that following the improved districtual circulation (the cicatricial area is usually poorly vascularized, contrary to what was believed up to now) and the fibroblast proliferation stimulation, a remarkable induction of a regular capillarogenesis takes place. The wound healing with the products of the present invention turned out to be accelerated and at the same time modulated. In bedsores and torpid ulcers, the larger blood flow to the necrotic area leads to a restoration of the tissue healing properties and a reduction and disappearance of the ulcer. Analogous results are obtained in the hemorrhoidal pathology, in which the simultaneous effect on arteries and veins allows a fast regression of venous stasis.

The treatment above described relates to the treatment of cauterized wounds and or healing wounds, or of cutaneous ulcers, or of venous stasis conditions. Further, it has surprisingly been found that the administration of a formulation containing 1% esculetin and 0.3% procyanidanole oligomers from *Camellia sinensis* on newly formed scars leads to a faster disappearance of the cicatritial outcome, with a remarkable reduction in the hyperhaemic area compared with the controls. The result of such a treatment is particularly important in the exposed body areas, where facial esthetic surgery, removal of naevi and the like are performed.

Moreover, it has been found that the above cited coumarins, alone or in combination with proanthocyanidins, are markedly effective in the treatment of atopic dermatitis and haematomas of any origin. Therefore, topical administrations of a formulation containing 2% esculetin on atopic dermatitis induce a reduction of the dermatitis within one week or less, depending on the severity and degree of the pathology. The same formulation, applied on haematomas, made them to disappear within a few days, probably as a result of the microvasculokinetic activity of the product.

Particularly useful as excipients for the formulations of the invention are the phospholipids, either pure or in the form of the natural mixtures thereof, which allow the quick absorption of the substances themselves, even though other excipients can advantageously carry the products of the invention, enhancing their therapeutical or dermocosmetic functionalities.

EXAMPLES

The formulations according to the invention contain, besides the above defined active principles, carriers, additives, preservatives and the like known in pharmaceutical technique, such as those listed in the examples reported hereinbelow, which illustrate the invention without limiting its scope. The formulations set forth in the examples were used in the treatments described above.

Example I

Gel containing esculoside and procyanidole oligomers from Vitis vinifera. 100 g of gel contain:

| | |
|---|---|
| Esculoside | 1.50 g |
| 96% Procyanidole oligomers | 1.50 g |
| Hydrogenated castor oil 40 (OE) (Cremophor RH40 - BASF) | 1.00 g |
| Propylene glycol | 1.50 g |
| Preservatives | 0.10 g |
| Hydroxyethyl cellulose (Natrosol 250 HHX - Aqualon) | 3.00 g |
| Purified water | q.b. a 100 g |

Example II

Alcoholic fluid gel containing esculoside and proanthocyanidin A2. 100 g of gel contain:

| | |
|---|---|
| Esculoside | 1.50 g |
| Proanthocyanidin A2 | 0.50 g |
| Hydrogenated castor oil 40 (OE) (Cremophor RH40 - BASF) | 5.00 g |
| Propylene glycol | 3.00 g |
| Carbomer 940 (Carbopol 980 - Goodrich) | 1.00 g |
| Ethanol 95° | 45.00 g |
| Phosphatidylcholine (Phospholipon 90- Natterman) | 1.60 g |
| Glyceryl 6 (OE) Caprilate/Caprinate (Softigen 767) | 15.00 g |
| Preservatives | 0.40 g |
| Butylhydroxytoluene | 0.05 g |
| α-Tocopherol | 0.20 g |
| Ascorbic acid | 0.30 g |
| Dimethicone copolyol (SF 1188 - General Electric) | 2.00 g |
| 10% Triethanolamine | 5.00 g |
| Purified water | q.s. to 100 g |

Example III

Cream containing esculoside and proanthocyanidin A2. 100 g of cream contain:

| | |
|---|---|
| Esculoside | 2.50 g |
| Proanthocyanidin A2 | 1.00 g |
| Hydrogenated castor oil 40 (OE) (Cremophor RH40 - BASF) | 2.00 g |
| Propylene glycol | 2.00 g |
| Carbomer 934 (Carbopol 934 P - Goodrich) | 0.50 g |
| Alkyl $C_{10-30}$-Acrylate (Carbopol 1382 - Goodrich) | 0.50 g |
| Ethanol 95° | 15.00 g |
| Preservatives | 0.40 g |
| Cetyl Palmitate (Cutina CP - Henkel) | 8.00 g |
| Polyisoprene (Syntesqual - Vevy) | 5.00 g |
| Polysorbate 80 (Tween 80 - ICI Americans) | 2.00 g |
| α-Tocopherol | 0.20 g |
| Ascorbyl palmitate | 0.10 g |
| Hydrogenated lanolin (Lanocerina - Esperis) | 5.00 g |
| Dimethicone 350 cps (Tegiloxan 350 - Tego) | 0.50 g |
| Phosphatidylcholine (Phospholipon 90- Natterman) | 2.50 g |
| 10% NaOH sol. | 2.40 g |
| Purified water | q.s. to 100 g |

Example IV

Gelified emulsion containing esculetin and procyanidanole oligomers from *Camellia sinensis*. 100 g of emulsion contain:

| | |
|---|---|
| Esculetin | 1.00 g |
| 96% Procyanidole oligomers | 0.30 g |
| Isopropyl myristate | 5.00 g |
| Preservatives | 0.40 g |
| Perfume | 0.10 g |
| Polyacrylamide, $C_{13-14}$-isoparaffin and lauric alcohol 7 (OE) (Sepigel 305 - Seppic) | 3.00 g |
| Purified water | q.s. to 100 g |

Example V

Gelified emulsion containing esculetin. 100 g of gelified emulsion contain:

| | |
|---|---|
| Esculetin | 2.00 g |
| Isopropyl myristate | 5.00 g |
| Preservatives | 0.40 g |
| Perfume | 0.10 g |
| Polyacrylamide, $C_{13-14}$-isoparaffin and lauric alcohol 7 (OE) (Sepigel 305 - Seppic) | 3.00 g |
| Purified water | q.s. to 100 g |

What is claimed is:

1. A topical pharmaceutical or cosmetic composition for increasing blood capillary density comprising about 1 to 2.5% by weight of at least one coumarin and about 0.3 to 1.5% by weight of at least one proanthocyanidin.

2. The composition of claim 1, wherein the coumarin is esculoside, esculetin, an extract containing esculoside or esculetin, or a mixture thereof.

3. The composition of claim 1, wherein the proanthocyanidin is proanthocyanidin A2, procyanidole oligomers extracted from *Vitis vinifera* or *Camellia sinensis*, or a mixture thereof.

4. The composition of claim 1, wherein the proanthocyanidin is proanthocyanidin A2.

5. The composition of claim 1, which further comprises at least one phospholipid as an excipient.

6. The composition of claim 1, wherein the weight ratio of coumarin to proanthocyanidin is about 4:1 to about 1:4.

7. The composition of claim 1, further comprising a carrier.

8. A method for increasing blood capillary density in a subject, which comprises topically applying a composition comprising at least about 1% by weight of at least one coumarin and at least about 0.3% by weight of at least one proanthocyanidin upon the subject in areas where increased blood capillary density is desired.

9. The method of claim 8, wherein the composition is applied to a subject having a condition selected from the group consisting of impaired arterial and venous circulation; unesthetisms; scars; hemorrhoids; chronic venous stasis; couperose; or peripheral capillaropathies.

10. The method of claim 8, wherein the coumarin is esculoside, esculetin, an extract containing esculoside or esculetin, or a mixture thereof.

11. The method of claim 8, wherein the proanthocyanidin is proanthocyanidin A2, procyanidole oligomers extracted from *Vitis vinifera* or *Camellia sinensis*, or a mixture thereof.

12. The method of claim 8, wherein the proanthocyanidin is proanthocyanidin A2.

13. The method of claim 8, wherein the coumarin and proanthocyanidin are applied with an excipient that comprises at least one phospholipid.

14. The method of claim 8, wherein the weight ratio of coumarin to proanthocyanidin in the composition is about 4:1 to about 1:4.

15. The method of claim 8, wherein the composition includes a carrier, and comprises between about 1 to 2.5% by weight of coumarin and between about 0.3 to 1.5% of proanthocyanidin.

16. The method of claim 8, further comprising applying the composition at least twice a day for up to about 60 days.

17. A method of treatment for atopic dermatitis and hematomas, comprising topically applying a composition comprising at least about 1% by weight of at least one coumarin and at least about 0.3% by weight of at least one proanthocyanidin to increase skin blood capillary density.

18. The method of claim 17, wherein the coumarin is esculoside, esculetin, extracts containing esculoside or esculetin, or mixtures thereof.

19. The method of claim 17, wherein the proanthocyanidin is proanthocyanidin A2, procyanidole oligomers extracted from *Vitis vinifera* or *Camellia sinensis*, or a mixture thereof.

20. The method of claim 17, wherein the composition comprises between about 1 to 2.5% by weight of coumarin and between about 0.3 to 1.5% of proanthocyanidin.

21. The method of claim 17, further comprising applying the composition at least twice a day for up to about 60 days.

22. The composition of claim 20, wherein the coumarin is esculoside or esculetin and the proanthocyanidin is proanthocyanidin A2.

23. A topical pharmaceutical or cosmetic composition for increasing blood capillary density consisting essentially of at least about 1% by weight of at least one coumarin and at least about 0.3% by weight of at least one proanthocyanidin.

* * * * *